United States Patent [19]

Gogolewski

[11] Patent Number: 4,834,747

[45] Date of Patent: May 30, 1989

[54] METHOD OF PRODUCING A MULTILAYERED PROSTHESIS MATERIAL AND THE MATERIAL OBTAINED

[75] Inventor: Sylwester Gogolewski, Renens, Switzerland

[73] Assignee: Medinvent S.A., Lausanne, Switzerland

[21] Appl. No.: 882,898

[22] PCT Filed: Oct. 28, 1985

[86] PCT No.: PCT/SE85/00420

§ 371 Date: Jun. 24, 1986

§ 102(e) Date: Jun. 24, 1986

[87] PCT Pub. No.: WO86/02843

PCT Pub. Date: May 22, 1986

[30] Foreign Application Priority Data

Nov. 8, 1984 [SE] Sweden ................................ 8405596

[51] Int. Cl.$^4$ ............................ A61F 2/00; B05D 5/00
[52] U.S. Cl. ........................................ 623/1; 623/901; 623/66; 427/2; 427/245; 264/41
[58] Field of Search .......................... 427/2, 246, 245; 264/41; 623/1, 66, 901

[56] References Cited

U.S. PATENT DOCUMENTS

| | | | |
|---|---|---|---|
| 3,526,224 | 9/1970 | Potts et al. | 128/156 |
| 3,546,004 | 12/1970 | Schachowskoy et al. | 427/246 |
| 3,813,466 | 5/1974 | Anderson | 424/444 |
| 4,135,011 | 1/1979 | Mimura | 427/246 |
| 4,173,689 | 11/1979 | Lyman et al. | 521/64 |
| 4,289,125 | 9/1981 | Hung | 128/156 |

FOREIGN PATENT DOCUMENTS 2802295 7/1978 Fed. Rep. of Germany.

*Primary Examiner*—Evan Lawrence
*Attorney, Agent, or Firm*—Burns, Doane, Swecker & Mathis

[57] ABSTRACT

A method of producing a mono- or multilayered prosthesis material for use with a living body, the material showing mechanical compliance vis-à-vis soft body tissue and possessing biocompatibility, the method comprising the steps of:
  (a) preparing a polymer solution using a mixed solvent, the solution being near its precipitation point;
  (b) coating a substrate and precipitating thereon the polymer to form a physically stable porous structure by evaporating at least part of the solvent fraction of the mixed solvent;

and the multilayered prosthesis material prepared by the method.

10 Claims, No Drawings

METHOD OF PRODUCING A MULTILAYERED PROSTHESIS MATERIAL AND THE MATERIAL OBTAINED

The present invention relates to the provision of a prosthesis material for use with a living body, the material produced showing mechanical compliance vis-à-vis soft body tissue and, furthermore, possessing biocompatibility. The invention includes a method for the manufacture of such material.

In using synthetic polymers as replacement material for various types of human tissue it is not only the biocompatibility properties of the polymer which is of critical importance to the performance of the material when used with a living body. In addition to biocompatibility and blood compatibility the mechanical compliance and porosity features are of basic importance. The available materials are not satisfactory in this respect. In other words, due to mechanical factors the applied material does not possess a mechanical performance which is in line with that of the surrounding natural tissue.

Accordingly, it is an object of the present invention to provide a prosthesis material of a synthetic nature showing mechanical compliance vis-à-vis soft body tissue at the same time possessing biocompatibility or blood compatibility.

Another object of the invention is to provide a prosthesis material for such use, which shows the desirable porosity in combination with mechanical resistance and compliance.

Yet another object of the invention is to provide a method for producing such prosthesis material, the method comprising a new feature of using a solvent of a special nature and a new precipitation technique in connection herewith.

Still another object is to provide a porous material of a fibrelike structure. In connection with extensive research and experimentation it has been found that a mono- or multilayered prosthesis material can be prepared starting from a solution of a copolymer in a mixed solvent and coating a substrate with a uniform thickness of such solution. The polymer is precipitated by evaporation and one or several consecutive layer(s) are applied to form a prosthesis material.

The invention is based on an entirely new concept of using a mixed solvent and a specific precipitation technique. The mixed solvent comprises as a first constituent a fluid which is miscible with the solvent but functions as a precipitating non-solvent with respect to polymer. Furthermore, the mixed solvent comprises a second constituent which is solvent for the polymer. In the polymer solution using a mixed solvent two criteria are of importance which will be further explained below.

The first criterion of the polymer mixed solvent solution is the feature that the solvent constituent thereof must have a higher rate of evaporation than the non-solvent constituent. The importance of this feature will be explained in the following.

The second criterion of the polymer mixed solvent solution is the feature that the degree of saturation thereof with regard to the polymer contents must be such that the polymer solution is near its precipitation point. By a saturation which is "near the precipitation point", is meant that the polymer solution used for preparing the mono- or multilayered material contains at least about 60% and preferably at least 80% by weight of the amount of polymer corresponding to a saturated solution of the same polymer in the same mixed solvent. It is preferred that the polymer solution used in the method of the invention contains no less than about 90% of the said amount of polymer.

In addition to these features of the polymer solution used for making the multilayered prosthesis material the invention also provides for a new precipitating technique which in principle resides in precipitating the substrate coating of the polymer solution by evaporating at least part of the solvent constituent or solvent fraction of the mixed solvent to precipitate the polymer to form a layer thereof on the substrate before applying another coating of polymer solution. Evaporation of the solvent constituent of the mixed solvent is facilitated by the fact that the solvent constituent is more voltaile than the non-solvent constituent of the mixed solvent.

Evaporation of the solvent fraction of the mixed solvent can be achieved in any suitable manner. Thus, evaporation can take place merely by autoevaporation into the surrounding air or it can be accelerated by heating, forced circulation, applying vaccum or using other conventional technique.

In accordance with the invention it is preferred to carry the evaporation of the solvent constituent to a point where some solvent constituent is left in each preceding layer when the subsequent layer is applied. It has been found, that if evaporation takes place in such manner repeating the procedure to form another layer of coating results in the formation of inter-phase fibers which form a mechanically strong linkage between the first layer and the subsequent layer. This will prevent progressive delamination of for example a graft wall when implanted in a living body. Such delamination is a disadvantage and generally results in the formation of extensive aneurysms upon implantation.

Although the invention is not limited to any specific theory or mechanism, there are different factors which might explain how the very strong linkage is achieved. It has thus been observed that there are many fibres in the boundary of two subsequent layers, which seem to be interlocked probably due to the fact that many tiny fibres in the outer surface of the first layer are partly dissolved in the mixed solvent system. As soon as the new fibres are precipitated in the subsequent evaporation step, also the partly dissolved fibres produced in the preceding step are reformed, thus giving an interlocking effect of the two subsequent layers. There are also fibres precipitated in the second subsequent layer, which are trapped in the pores of the first layer. At last there may also be a kind of glueing effect between fibres in the outer surface of the first layer and the inner surface of the second layer. This results from the presence of small amounts of solvent left in the precipitated polymer.

There are, of course, alternative procedures for preparing a polymer solution using a mixed solvent which is near its precipitation point. One such alternative which is a simple one for use in actual practice is as follows. A solution of polymer is prepared using a solvent, for example tetrahydrofuran. To this clear polymer solution there is added a precipitating agent or non-solvent, for example water, until a slight cloudiness is obtained. Then tetrahydrofuran is added to the cloudy solution until a clear solution is again obtained and this clear solution is useful for coating a substrate and meets the requirements of this invention in regard to nearness to the precipitation point.

According to the present invention it has been found that by using the technique outlined above a polymer layer when precipitated will be obtained which has a fibre-like structure the pores of which are interconnected. The precipitated fibrelike material consists of fibres of different thickness from tiny fibres to relatively thick ones. Each precipitated layer has a thickness of for example about 0.01 to 1 mm and up to about 100 and even more layers may be applied in subsequent operations to produce a multilayered prosthesis material of the required mechanical strength. Due to the fiberlike porous structure the prosthesis wall is strong, highly compliant and mechanically compatible with the tissue to be replaced.

Although the polymer concentration of the mixed solvent solution is not critical for obtaining useful results it is preferred to use a solution containing less than about 5% by weight of polymer. Sometimes the concentration can be less than about 3% of polymer and in some cases even concentrations as low as about 0.5% or less may be useful.

In connection with or after coating the substrate with the polymer solution the coating applied is precipitated by evaporating at least part of the solvent fraction of the mixed solvent. The procedure is then repeated as desired to form a multilayered product.

It has been found that the pore size is very much dependent on the concentration of the polymer solution. An example of relationship between pore size and polymer concentration for a specific copolyurethane is given below.

| Concentration % by weight | Average pore size micron |
|---|---|
| 0.20 | 300–500 |
| 1.00 | 100–300 |
| 1.25 | 50–150 |
| 1.45 | 35–60 |
| 2.00 | 30–50 |
| 4.00 | 5–15 |

By using the multilayer precipitating technique according to the invention and described above, it is possible to produce a multilayer prosthesis wall for tissue replacement with different pore size in the different layers. For example in a vascular porsthesis it is possible to produce the inner layers e.g. the layers of the lumen of the prosthesis with a relatively small pore size (5–10 microns) to enhance endothelization but the center and the outer layers with a relatively large pore size (30–100 microns) to ensure a good tissue ingrowth.

In the method of the present invention the polymer used for preparing the solution for coating the substrate can be any polymer useful in the context, but it is preferred to use a copolyurethane, particularly a block or segmented copolyurethane.

The technique of this invention permits easy production of multilayered products with different average pore sizes of the individual layers. This is done by varying the concentration of polymer in the casting solution, i.e. the solution to be applied onto the substrate. This is useful for example for the preparation of a vascular prosthesis, where it is desired to have the lumen face of prosthesis with a much lower pore size, such as within the range about 5 to 15 μm. This is to facilitate endothelization after implantation. On the other hand it is desired that the remaining part of the prosthesis wall has larger pores to allow faster tissue ingrowth.

As a solvent there may be used any solvent having the ability to dissolve the polymer used, but preferred solvents are those selected from the group consisting of tetrahydrofurane, amide solvents and sulfoxide solvents. Among such solvents there may be mentioned in addition to tetrahydrofuran (THF) dimethylacetamide (DMAc), dimethylformamide (DMF) and dimethylsolfoxide (DMSO). Particularly preferred is a mixed solvent of THF and DMF.

As a non-solvent there may be used any fluid having the capacity to precipitate the polymer. A preferred solvent is water but also lower alkanols, such as ethanol, may be used, optionally in combination with water.

The polymer used in forming the solution should be biocompatible and elasticity is preferred in some applications, such as use in vascular prosthesis. The polymer can be natural or synthetic. Examples of the former are polyaminoacids (e.g. polyglycin), polysaccharides (e.g. cellulose derivatives, alginates). Examples of synthetic polymers are silicones and polyurethanes. Mixtures of various polymers can also be used.

As previously indicated segmented aliphatic polyurethanes or segmented aromatic polyurethanes may be used in applying the technique of this invention. In order to obtain materials which are non-toxic, non-mutagenic and non-carcinogenic it is preferred to use segmented aliphatic polyurethanes or using another expression aliphatic block copolymers.

The polymeric material for use in the invention may be conventionally prepared from aliphatic polyurethanes based on diisocyanates, e.g. 1,2-diisocyanatoethane, 1,5-diisocyanato pentane, hexamethylene diisocyanate, methane diisocyanato pentane, 1,9-diisocyanato nonane, 1,8-diisocyanato octane, 1,4-diisocyanato butane, 4,4'-methylenebiscyclohexyl diisocyanate, lysine diisocyanate, 1,4-transcyclohexane diisocyanate, dimethyldiisocyanato silane, diethyldiisocyanato silane. In addition to such diisocyanates there may be used polyols having average molecular weight within the range of 500 to 10000, e.g. poly(ethylene adipate), poly(tetra-methylene adipate), poly(1,4-cyclohexyldimethylene adipate), poly(hexamethylene oxalate), poly(hexamethylene glutarate), poly(E-aprolactone), poly(tetramethylene oxide), poly(ethylene oxide), poly(1,2-propylene oxide). Chain extenders e.g. 1,4-butandiol, 2,4,6-tris(dimethylaminomethyl)-phenol glycerol, 3,6-dioxaoctane 1,8-diol, ethylene diol, diethylene diol, tetramethylene diamine, ethylene diamine, hexamethylene diamine, propylene diamine.

The copolyurethanes are conventionally formed by e.g. reacting a prepolymer such as a polyether diol, with a diisocyanate, and the product resulting from such reaction may then be chain extended by reacting with a diol or diamine. By such polymerization process copolymers may be produced having preferred molecular weights and preferred viscosity in solution. By varying the molecular weight and thus the viscosity of the polymer in solution the rate of degradation and porosity of the material prepared may be controlled.

The selected polymer material is dissolved in a suitable solvent of the type indicated above and the proportions between polymer and solvent are suitably selected so as to give the desired percentage of solids in the resulting solution. The coating solution is then used to coat a substrate to form an initial coating of uniform thickness. As a substrate there may be used any mechanical means of suitable type, such as a metal plate or a metal mandrel, preferably coated with a resistant plastic, such as polytetrafluoro ethylene. The coating can be provided by spraying, extrusion, immersion or dipping or in some other conventional manner.

The multilayered prosthesis material of the present invention can be used in a multitude of medicinal applications. Thus, it can be used as a vascular graft, as a skin graft or as a wound dressing. Moreover, it can be used as elastic membranes for ear drum replacement, as elements for orthopedic surgery and as anticoagulent tubing for blood transfusion.

For use in a graft or a wound dressing a multilayered composite material can be choosen, where the inner and/or the outer layer consists of a porous degradable polymer, e.g. polyhydroxybutyrate or a polysaccharide to enhance endotheliation and epitheliation respectively.

The invention will now be further described by specific examples which, however, must not be construed to limit the scope of the invention.

EXAMPLE I—General procedure

Preparation of casting solution

Segmented polyurethane was dissolved in dimethylformamide (DMF) at 23° C. (2 wt-%) solution and then precipitated with water to remove the oligomeric fractions thereof.

Precipitated polymer was dried to constant weight and then dissolved in tetrahydrofuran (THF). The concentration of polymer in solution was in the range of 0.1–4 wt-%, being dependant on the purpose of the use of the solution. In general, more concentrated solutions are required for preparation of reinforced vascular prostheses while more dilute solutions are needed for the preparation of e.g. wound dressings or artificial skins.

The resulting polymer solution was heated to 25° C. and water was then added dropwise while the solution was stirred vigorously.

The amount of water which can be added to the polymer solution at the given temperature without causing the polymer to precipitate is dependant inter alia on the molecular weight and the molecular weight distribution of the polyurethane used and the concentration of polymer in the solution.

In general less water (non-solvent) can be added to a solution prepared from a polmer of high molecular weight and broader molecular weight distribution.

The presence of water in the polymer solution affects the propsity of the resulting product. It has been found, that the more water is added to the polymer solution, the larger the pores formed.

From the polyurethane solutions described in this example, various medical goods can be produced e.g. vascular prostheses, wound dressings, microporous patches etc. These products can be produced using commonly used techniques, e.g. dip-coating, spraying, painting, brushing, blade-coating, etc.

The products can be prepared in one operation or in several similar operations, e.g. for the preparation of vascular prostheses composed of several layers of varying porosites.

Applying the polymer solution to the substrate results in fast precipitation of polymer which is due to evaporation of solvent from the polymer-solvent-non-solvent ternary system.

It has been found to be preferred that after depositing the polymer layer on the substrate, excess of solvent is dried or pressed out from the layer, before the subsequent layer is deposited on the previous one. This measure contributes to the formation of strong mechanical binding betwen the layers forming the structure of the product and assists in avoiding separation of the layers upon implantation.

EXAMPLE II

Preparation of vascular prostheses

Polyetherurethane prepared according to the procedure outlined in Example I above with a molecular weight of $1.0 \times 10^5$ was dissolved in tetrahydrofuran to prepare a solution with a concentration of about 2 wt-%.

The polymer solution was heated to about 25° C. and then about 20 wt-% of water (based on a total volume of solvent) was added to the solution under stirring.

Stainless steel bars covered with polytetrafluoroethylene (PTFE) were dip-coated with the polymer solution, and about 5 minutes later excess of solvent-non-solvent residue was removed from the polymer precipitate by applying to the polymer layer an absorbing paper. The dip-coating procedure was repeated 40 times to produce a composite, mechanically strong and highly elastic vascular prosthesis.

The prostheses on the moulds were soaked for 16 hours in deionized water, were then removed from the mould and soaked again for 5 hours. The prostheses were dried at 40° C. in a vacuum oven before sterilization with ethylene oxide.

Prostheses prepared in this manner when implanted in pigs show satisfactory low thrombogenic activity, fast endothelialization and regular tissue ingrowth.

EXAMPLE III

Preparation of a microporous patch (artificial dermis)

A polyesterurethane with an average molecular weight of $3.0 \times 10^5$ based on hexamethylene diisocyanate, poly(ethylene adipate) and 14-butadiol was dissolved in a mixture of tetrahydrofuran-dimethyl-formamide (9.8/0.2 vol/vol) to produce a polymer solution with a concentration of polymer of 0.7 wt-%. The polymer solution was stirred, heated to 28° C. and then 20 vol-% of water (calculated on the total amount of solvent) was added dropwise to the solution.

The polymer solution was sprayed against polished PTFG plates. The resulting macroporous patches were finally soaked for 16 hours in deionized water and subsequently dried.

The macroporous patches with a porosity in the range of 100–150 μm were used to cover full thickness skin wounds. It was found that this treatment stimulates the healing process of non-infected wounds.

EXAMPLE IV

Artificial skin

Polyetherurethane based on hydrolytically stable cycloaliphatic diisocyanate (Texoflex ®-80a) was dissolved in a tetrahydrofuran-water mixture (99/1 vol/vol) at 30° C. The concentration of polymer in the mixture was 0.75 wt-%.

The polymer solution was sprayed against the microporous polyurethane patch described in Example III.

As a result of spraying, a bilayer membrane was formed composed of an upper protective layer with a porosity in the range of 0.4–0.9 μm and a sublayer with a porosity in the range of 100–150 μm.

This composite membrane is nontoxic, nonmutagenic and noncarcinogenic.

The bilayer membrane was used to cover donor sites and full-thickness skin wounds of guinea-pigs. It is found that the membrane protects satisfactorily against bacterial invasion and assures proper water and gas transport to and from the wound. The use of the membrane facilitates the healing process of non-infected wounds of guinea-pigs.

I claim:

1. A method of producing a multilayered prosthesis material for use with a living body, said material showing mechanical compliance vis-a-vis soft body tissue and possessing biocompatibility, said method comprising the steps of
   (a) preparing a solution of a biocompatible polymer using a mixed solvent, the mixed solvent including as a first constituent a solvent in which said polymer is substantially dissolvable and as a second constituent a non-solvent in which said polymer is not substantially dissolvable, said solvent and said non-solvent being substantially miscible, and said solution being near the precipitation point of said polymer;
   (b) applying said solution to a substrate, thereby forming a coating of said solution on said substrate;
   (c) precipitating the polymer in said coating by evaporating only a portion of the solvent, the amount of evaporation being such that said solution reaches the precipitation point of said polymer, the precipitate forming a physically stable porous structure, and
   (d) repeating steps (a), (b) and (c) in sequential fashion to form a plurality of coatings on said substrate, thereby forming the multilayered prosthesis material, said material being usable as a prosthesis when removed from said substrate.

2. The method according to claim 1, characterized by using a copolyurethane as the polymer in step (a).

3. The method according to claim 2, wherein the polymer is a segmented copolyurethane.

4. The method according to claim 1, wherein the solvent is selected from the group consisting of tetrahydrofuran, amide solvents and sulfoxide solvents.

5. The method according to claim 1, wherein the non-solvent is selected from the group consisting of water and lower alkanols.

6. The method of claim 1, wherein the concentration of polymer in each of the plurality of solutions prepared according to step (a) is varied, thereby producing a multilayered material wherein the different layers have different average pore sizes.

7. The method of claim 1, wherein the solution prepared in step (a) contains less than about 5% by weight of polymer.

8. The method of claim 1, wherein the solution prepared in step (a) contains less than about 3% by weight of polymer.

9. The method of claim 1, wherein said solvent has a higher rate of evaporation than said non-solvent.

10. Prosthesis material prepared by the method of claim 1.

* * * * *